United States Patent [19]

Tada et al.

[11] Patent Number: 5,126,259
[45] Date of Patent: Jun. 30, 1992

[54] HUMAN B. LYMPHOBLASTOID CELL, HYBRIDOMA, ANTIBODY AND PRODUCTION OF ANTIBODY

[75] Inventors: Hiroko Tada, Kawanishi; Yukio Toyoda, Amagasaki; Atsushi Kakinuma, Nagaokakyo, all of Japan

[73] Assignee: Takeda Chemical Industries, Ltd., Osaka, Japan

[21] Appl. No.: 286,761

[22] Filed: Dec. 19, 1988

[30] Foreign Application Priority Data

Dec. 24, 1987 [JP] Japan .................. 62-328841

[51] Int. Cl.⁵ ............................... C12N 5/12
[52] U.S. Cl. .................................. 435/240.2
[58] Field of Search ............ 435/240.2, 240.27, 172.2; 530/387; 935/100

[56] References Cited

FOREIGN PATENT DOCUMENTS 0176365 9/1985 European Pat. Off. .
60-203186 10/1985 Japan .
8607382 12/1986 PCT Int'l Appl. .

OTHER PUBLICATIONS

Chemical Abstracts, 100:207654v.
Ichimori et al., Biochemical and Biophysical Research Communications, vol. 142, No. 3, 1987, pp. 805-812.
Y. Shintani et al.; Text for Fourth Symposium on Research and Development Project of Basic Technology for Future Industries, p. 51 (1986).
Chemical Patents Index, Country Alerting Bulletin, Section, D, 88-143402/21 J63084-488-A.

Primary Examiner—John Doll
Assistant Examiner—Susan L. Futrovsky
Attorney, Agent, or Firm—David G. Conlin; Linda M. Buckley

[57] ABSTRACT

The present invention provides human B lymphoblastoid cell line AC-33, which is novel, and excellent in proliferativity and fusion capability, and works well as the parental line for obtaining a human monoclonal antibody-producing hybridoma. Said hybridoma possesses excellent proliferativity and stable antibody productivity, thus permitting efficient antibody production over a long period.

1 Claim, 1 Drawing Sheet

HUMAN B. LYMPHOBLASTOID CELL, HYBRIDOMA, ANTIBODY AND PRODUCTION OF ANTIBODY

BACKGROUND OF THE INVENTION

The present invention relates to an antibody-producing hybridoma, antibody, and a method of antibody production.

The method for producing monoclonal antibody (hereinafter also abbreviated MoAb) using a hybridoma, developed by Köhler and Milstein, is advantageous in that a monospecific antibody can be obtained in large amounts and stably; it is widely applied to various fields [Köhler, G. and Milstein, C.; Nature, 256, 495 (1975)]. In particular, it has recently been making great contributions to the development of new preventive and therapeutic drugs as well as to the detection and purification of antigens and development of diagnostics.

However, in administering mouse MoAb, a protein foreign to humans, as a preventive and/or therapeutic drug, there is a risk that the therapeutic effect may be attenuated as a result of production of an antibody against mouse MoAb in human bodies; as well, serious allergic reaction may result. Therefore, human MoAb is much more desirable for use as a preventive and/or therapeutic drug, but human MoAb preparation lags far behind mouse MoAb preparation in technical advancement, with only a few successes in actual preparation. Human MoAb is produced using human-human hybridomas, mouse-human hetero hybridomas and Epstein-Barr virus (hereinafter also abbreviated EBV) transformants of human lymphocytes etc. Since the latter two are inferior to the former in stability of antibody production and proliferativity, it is desired that human MoAb be produced using a human-human hybridoma. However, the fusion efficiency in the preparation of human-human hybridomas is generally very low, which considerably retards the development of human MoAb as a pharmaceutical. To overcome this drawback, parental lines have been under development which are excellent in proliferativity and which can be fused with a human lymphocyte at high efficiency; Yamada et al. established the HO-323 cell line [Yamada, K. and Murakami, H.; Fermentation and Industry (in Japanese), 45, 218 (1987)] and Ichimori et al. the TAW-925 cell line [Ichimori, Y., Harada, K., et al.; Biochemical and Biophysical Research Communications, 142, 805 (1987)]. At present, however, there is urgent need for development of a parental line which will yield a human-human hybridoma possessing stable antibody productivity and excellent proliferativity, and which can be fused with a human lymphocyte to prepare said hybridoma at still higher efficiency.

The purpose of the present invention is to provide a human-human hybridoma which produces an antibody stably and which possesses excellent proliferativity, a method of antibody production using said hybridoma, and the antibody produced by said hybridoma.

DETAILED DESCRIPTION

Figure 1:
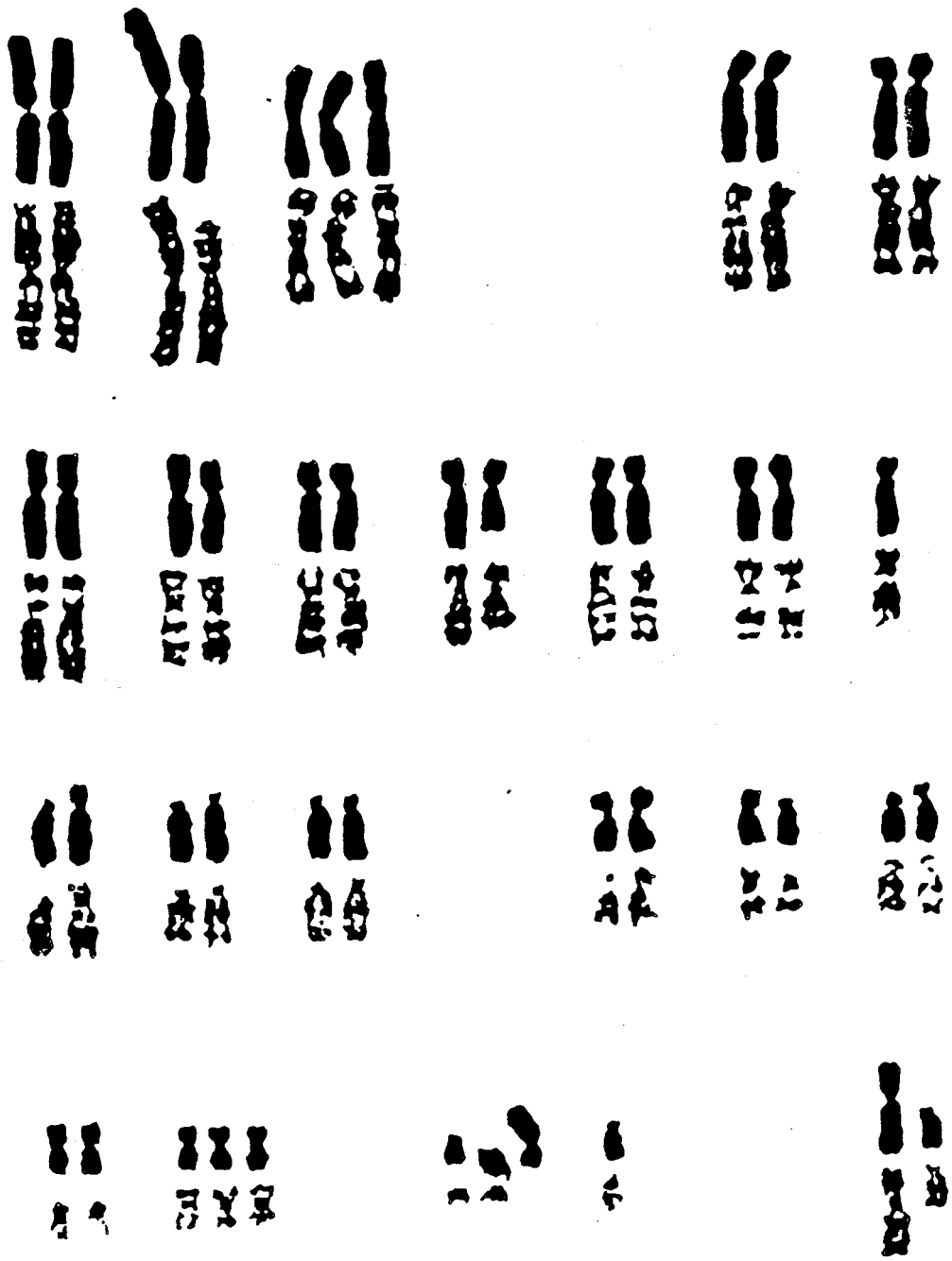
FIG. 1 shows the chromosome map of the AC-33 line as obtained in Reference Example 1.

With this technical background, the present inventors made intensive studies with the aim of preparing a human-human hybridoma which stably produces a human monoclonal antibody possessing high binding affinity to human cancer cells or *Pseudomonas aeruginosa* exotoxin A (hereinafter also abbreviated PEA), and found that the human B lymphoblastoid cell line AC-33 (hereinafter also referred to as AC-33 line), an ouabain-resistant cell line (obtained by adapting, stepwise, the 6-thioguanine (6-TG)-resistant human B lymphoblastoid cell line WI-L2 (supplied by Dr. G. Sato of the Alton Jones Cell Science Center, USA) to the presence of ouabain in the culture medium), fuses with an EBV transformant at high efficiency to yield a hybridoma possessing excellent proliferativity, which can thus serve well as a parental line for obtaining a human MoAb-producing hybridoma.

The present inventors also found that a human-human hybridoma which stably produces an anti-human cancer cell human MoAb or anti-PEA human MoAb can be realized by fusing an EBV transformant (which produces said antibody) with the AC-33 line, and that an anti-human cancer cell or anti-PEA human MoAb can be produced from said hybridoma. The inventors made further investigations based on these findings and developed the present invention. Throughout the present specification as well as claims, an anti-human cancer cell human MoAb means a human MoAb reactive to human cancer cells, and an anti-PEA human MoAb means a human MoAb reactive to PEA.

Accordingly, the present invention relates to (1) human B lymphoblastoid cell line AC-33 or its subculture lines, (2) a hybridoma formed between human B lymphoblastoid cell line AC-33 or its subculture lines and a human lymphocyte transformed with EBV, (3) a method of human MoAb production characterized by cultivation of said hybridoma in medium and subsequent antibody collection, and (4) the human MoAb produced by said hybridoma. Human B lymphoblastoid cell line AC-33 is sensitive to HAT (hypoxanthine, aminopterin, thymidine) and resistant to ouabain, and it can, e.g., be prepared by improving the 6-TG-resistant human B lymphoblastoid cell line WI-L2 (supplied by Dr. G. Sato at the Alton Jones Cell Science Center, USA). A HAT-sensitive, ouabain-resistant cell line can usually be prepared by a known method. The present inventors have obtained a new cell line which is sensitive to HAT and resistant to ouabain without affecting the proliferativity inherent in the present line, e.g. by adapting a human-derived lymphoblastoid cell line under cultivation to gradually increased concentrations of 6-TG and ouabain in the medium.

To describe in detail the method of obtaining such a cell line: 6-TG-resistant human B lymphoblastoid cell line WI-L2 is cultivated in a medium containing ouabain at a concentration of below 0.01 $\mu$M, preferably 0.002 to 0.005 $\mu$M, and ideally of 0.003 $\mu$M; the cells thus obtained are screened for cells which are not human immunoglobulin secretors. The line thus obtained which is not an immunoglobulin secretor and which is resistant to low concentrations of ouabain is further cultivated in a medium containing an increased concentration of ouabain, i.e., at a concentration of about 1.5 to 5 times, preferably 1.5 to 3.5 times, ideally about 1.5 to 2 times, in the early stage of adaptation, and then about 2 to 3.5 times that of the starting concentration, to thereby breed a cell line which is not an immunoglobulin secretor and which exhibits strong resistance specifically to ouabain, preferably to an over 2 $\mu$M concentration of ouabain. The cell line thus obtained can be used as the parental line for cell fusion with a human antibody-producing cell, preferably using a cell line giving a particularly high fusion efficiency, previously selected by cloning, etc.

As stated in Example 1 (1) below, the human B lymphoblastoid cell line AC-33 as obtained by selecting non-human immunoglobulin secretor cells through cultivation in a medium containing ouabain at a concentration increased stepwise from a low level to 2 µM, is a cell line exhibiting non-immunoglobulin secretor property, HAT sensitivity and ouabain resistance, and which has the new chromosome composition shown in FIG. 1. In addition, said AC-33 line surpasses the conventional parental lines, such as HO-323 and TAW-925, in fusion efficiency in human-human hybridoma preparation. Furthermore, the human-human hybridoma obtained possessing stable capability of human MoAb production and excellent proliferativity.

As to the subculture lines, mention may be made of all lines derived from the AC-33 line, including clone lines with good fusion efficiency obtained by cloning as well as simply by subculturing the AC-33 line.

As antibody-producing human lymphocytic cells to fuse with AC-33 or its subculture lines, lymphocytes derived from normal humans or patients can be used; for example, when the desired antibody is against a derivative of an infectious substance such as PEA, lymphocytes derived from a human infected with said substance may be used. These human lymphocytes may be derived from spleens, lymph nodes or peripheral blood, though lymphocytes derived from peripheral blood or lymph nodes are preferable. These lymphocytic cells may be used directly, or for fusion with the AC-33 line after stimulation and activation in vitro with an antigen or B lymphocyte mitogen (e.g. poke-weed mitogen, *Staphylococcus aureus* Kowan I). It is preferable that the human lymphocytes collected be infected with EBV and immortalized, and the desired antibody-producing cells subsequently being selected and concentrated for fusion with the AC-33 line. As described above, an antibody-producing hybridoma can be obtained more efficiently by the method using an EBV transformant; examples of usable EBV-containing liquid include the culture supernatant of the marmoset cell line B 95-8 [Proceedings of National Academy of Science, USA, 70, 190 (1973)].

In preparing an EBV virus transformant, human lymphocytes are suspended in medium to a concentration of about 0.5 to $5 \times 10^7$ lymphocytes/ml, preferably about $1 \times 10^7$ lymphocytes/ml; an appropriate amount of the above-mentioned culture supernatant of B 95-8 is added thereto. Infection is then carried out by slight shaking at about 37° C. for about 1 hr; this is followed by cultivation at about 37° C. for 5 to 30 days to obtain the desired EBV transformant of human lymphocyte.

For fusing the AC-33 line and the EBV transformant, a mixed suspension of these cells is treated by the addition of a fusogen such as Sendai virus or polyethylene glycol (PEG) or electric stimulation or by other methods known to those skilled in the art. In a preferred embodiment the cells are treated with PEG. PEG with a degree of polymerization of about 1,000 to 6,000, at a concentration of about 10 to 80%, is generally used; incubation time is about 0.5 to 30 minutes. Preferably, about 35 to 55% PEG 6,000 is used to treat the cells at about 37° C. for 5 to 10 minutes. Selection of fused cells can be achieved using a medium supplemented with HAT and ouabain (HATO medium) following conventional procedures; the parental lines are killed through this process. The culture supernatant of the hybridoma which has proliferated is subjected to antibody titration, whereby cells positive for antibody activity are selected.

For determining anti-human cancer cell MoAb, various methods known to those skilled in the art can be used; examples include the mixed hemagglutination (hereinafter also abbreviated MHA) method, in which the MoAb is detected by the adsorption of indicator erythrocytes to tumor cells, and the cell-ELISA method, in which the MoAb bound to tumor cells adhering to a microplate is detected by enzyme immunoassay (hereinafter also abbreviated ELISA). For determining anti-PEA MoAb, ELISA using a microplate on which PEA is adsorbed as the solid phase antigen is preferably used. The hybridoma positive for the antibody activity is immediately subjected to cloning, which can easily be carried out, usually by limiting dilution analysis etc. The culture supernatant of the cloned human-human hybridoma cells is assayed for antibody titer by any one of the above-mentioned methods, and a hybridoma stably producing an antibody with a high titer is selected, whereby the desired monoclonal hybridoma can be obtained.

It is possible to produce an human MoAb by allowing a hybridoma derived from AC-33 line or its subculture lines of the present invention to produce and accumulate the antibody, which is then collected.

The production and accumulation of said antibody is achieved by cultivating the hybridoma of the present invention. Cultivation is normally conducted in liquid medium or in the abdominal cavity of an animal (usually a mammal, such as the nude mouse). Examples of cultivation in liquid medium are described below.

Examples of the medium include basal media for animal cell cultivation [Iskove medium-Ham F12 medium 1:1 mixed medium (I.H medium), RPMI 1640 medium or other conventional supplements] as supplemented with fetal bovine serum etc. and GIT medium (commercially available from Wako Pure Chemical Industries, Ltd., Japan), a mammalian serum-derived composition for animal cell cultivation, produced by subjecting mammalian serum to purifying treatment including an inactivation process for contaminant micro-organisms and a salting-out/desalting process; cf. the gazette for Japanese unexamined patent publication No. 145088/1985, which corresponds to EP 0148770). GIT medium in particular is used advantageously with respect to the antibody purification described below.

Cultivation is normally carried out at about 30° to 38° C., preferably about 37° C., for 3 to 60 days, preferably 5 to 10 days.

Purification of the antibody in the culture broth can be achieved by techniques known to those skilled in the art.

For example, the cell culture broth is centrifuged to separate the culture supernatant, which is then collected and subjected to salting-out (usually with ammonium sulfate). The protein precipitate thus obtained is dissolved in an appropriate solution and dialyzed, after which it is subjected to column chromatography (ion exchange column, gel filtration column, etc.), whereby the desired antibody can be separated and purified. For example, about 30 mg of anti-human cancer cell MoAb with a purity of over 95%, as calculated in protein weight ratio, can be obtained from 6 l of the culture supernatant by the above procedure of separation and purification. In addition, standard samples of this purified antibody comprise less than about 0.1% of the contents of bovine serum albumin and bovine serum globulin, both foreign proteins, and are free of the possibility of EBV contamination; these features are favorable when the standard sample is administered to humans.

The human MoAb thus obtained may be subjected to proteolytic enzyme (papain, pepsin, etc.) treatment, reducing agent treatment, etc. thereby yielding an Fab, Fab', or F(ab')$_2$ fragment etc., which possesses binding affinity to human cancer cells or PEA, all of which can be used for the same purpose as the human MoAb of the present invention.

The anti-cancer cell human MoAb produced in accordance with the present invention specifically recognizes the tumor-associated antigen on the surface of tumor cells and binds to these cells, but not to normal cells. Also, the anti-PEA human MoAb produced in accordance with the present invention specifically recognizes the antigen determinant of PEA molecule, exhibiting strong binding activity to PEA. Said antibodies are very suitable for use as biochemical preparations, since they are homogeneous and potent. For instance, after germ removal by filtration with a membrane filter etc., they may be prepared as injections per se or by mixing a therapeutically effective amount of them with an appropriate pharmacologically acceptable carrier, excipient, diluent and so forth. Its administration dose varies according to the object diseases, the severity of diseases and the administration route. For example, when it is intravenously injected into patients with infectious diseases, it is used at the dose of about 0.01 to 50 mg/kg/day, preferably 0.1 to 2 mg/kg/day.

The human monoclonal antibody preparations thus obtained are suitable for cancer-associated antigen analysis, blood antigen detection and as diagnostics, and can also be administered as preventive and/or therapeutic drugs to mammals, for example, mice, rats, cats, dogs, swine, bovines, horses, monkeys, humans, etc.

Anti-human cancer cell human MoAb, particularly in use as anticancer agents, is expected to serve as carriers for proper anticancer agents, i.e. missile therapy agents, to be administered to cancer patients for treatment of cancer, as well as antitumor agents based on their own antitumor effect. In addition, anti-PEA human MoAb, as therapeutic drugs for infectious diseases, is superior to conventional polyclonal human immunoglobulin preparations in stability and safety, thus affording great therapeutic effect.

As stated above, being derived from humans, the human MoAb of the present invention is extremely low in anti-human antigenicity and toxicity, as compared with antibodies derived from foreign animals, such as mice and rats; as well, it exhibits hardly any side effects, permitting its administration directly to humans for preventing and/or treating diseases. In addition, since the human MoAb is produced from a specified established cell line, the possibility of contamination with unknown biohazards is lower than that with conventional immunoglobulin preparations, which are produced from peripheral blood collected from a large number of unspecified humans. Furthermore, the hybridoma which produces said human MoAb is capable of producing the human MoAb stably in vitro, thus permitting stable mass production of the human MoAb with high binding affinity and neutralizing capability, and constant quality.

Furthermore, providing a high fusion efficiency, the new human B lymphoblastoid cell line AC-33, used for the present invention, can be advantageously used to prepare an human MoAb-producing hybridoma which possesses excellent proliferativity and stable antibody productivity, thus permitting efficient antibody production over a long period.

Accordingly, the present invention provides the new human B lymphoblastoid cell line AC-33, which provides high fusion efficiency in preparing human-human hybridoma.

EXAMPLES

The present invention will now be described in more detail by means of the following reference examples and working examples, though the present invention is not by any means limited to these examples.

Note that human B lymphoblastoid cell line AC-33, disclosed in Example 1, has been deposited at the Institute for Fermentation, Osaka (IFO), Japan under accession number IFO 50155, since Dec. 14, 1987; it has also been deposited at the Fermentation Research Institute, Agency of Industrial Science and Technology, Ministry of International Trade and Industry, Japan (FRI), 1-3, Higashi 1-chome, Tsukuba, IBARAKI 305 JAPAN under the accession number FERM P-9788 since Dec. 24, 1987, the deposit being converted to a deposite under the Budapest Treaty, and has been stored at the FRI under the accession number FERM BP-2143.

The human-human hybridoma PA-10.1, disclosed in Example 5, has been deposited at the IFO, under the accession number IFO 50158, since Dec. 14, 1987, and at the FRI under the accession number FERM P-9791 since Dec. 24, 1987, the deposit being converted to a deposit under the Budapest Treaty, and has been stored at the FRI under the accession number FERM BP-2146.

The human-human hybridomas Ku102 and Ku105, disclosed in Example 7, have been deposited at the IFO under the respective accession numbers IFO 50156 and IFO 50157, since Dec. 14, 1987; they have also been deposited at the FRI under the respective accession numbers FERM P-9789 and FERM P-9790 since Dec. 24, 1987, the deposit being converted to a deposit under the Budapest Treaty, and has been stored at the FRI under the respective accession numbers FERM BP-2144 and FERM BP-2145.

REFERENCE EXAMPLE 1

Mixed Hemagglutination (MHA)

① Preparation of indicator cells using human erythrocytes

In the case of IgG antibody detection, anti-D antibodies were added to 2% human erythrocytes in suspension in a phosphate buffer solution (hereinafter also abbreviated PBS), followed by 3 hr incubation at room temperature. The mixture was washed with PBS and again suspended in a 2% suspension. To this suspension, goat anti-human IgG antibodies were added, followed by incubation at room temperature overnight. The mixture was then washed three times with PBS and the cells used as indicator cells.

In the case of IgM antibody detection, dried guinea pig complements were added to 2% human erythrocytes in suspension in PBS, and the cells immediately used as indicator cells.

(2) Target tumor cells were seeded on a Nunc Terasaki Plate at 1,000 to 2,000 cells per well, followed by one day of cultivation at 37° C. in a carbon dioxide incubator. After plate washing with PBS supplemented with 2% fetal calf serum (hereinafter also abbreviated FCS), the subject culture supernatant of hybridoma was added, followed by 1 to 2 hr of incubation at room temperature. The plate was then washed with PBS supplemented with 2% FCS; a 0.2% suspension of the indicator cells prepared in (1) above was then added dropwise to the plate in the amount of one drop per well. Reaction was further carried out at room temperature for 1.5 to 2 hr, when the plate was again washed with PBS supplemented with 2% FCS; hemadsorption to the tumor cells was then assessed microscopically.

REFERENCE EXAMPLE 2

Cell-ELISA Using Tumor Cells

Target tumor cells were seeded on a Nunc 96-well microplate at 10,000 to 40,000 cells per well, followed by one day of cultivation at 37° C. in a carbon dioxide incubator. After removal of the culture supernatant, another culture supernatant of an anti-cancer cell antibody-producing hybridoma was added; reaction was then carried out at room temperature for 2 hr. After microplate washing with a medium supplemented with 0.2% bovine serum albumin (hereinafter also abbreviated BSA), goat anti-human IgG antibodies labeled with horseradish peroxidase (hereinafter also abbreviated HRP) were added. Further reaction was carried out at room temperature for 2 hr. After microplate washing, a 0.1M citrate buffer solution containing orthophenylenediamine (as the enzyme substrate) and $H_2O_2$ was added to each well; enzyme reaction was then carried out at room temperature. Following reaction termination by 1N sulfuric acid, the amount of coloring pigments was determined at a wavelength of 492 nm by means of a Multiscan (Flow Co.).

REFERENCE EXAMPLE 3

ELISA For Determining The Anti-*Psuedomanas Aeruginosa* Exotoxin A (PEA) Antibody A 2.5 μg/ml solution of PEA was dispensed in a 96-well microplate at 100 ml per well; the microplate was then left at 4° C. for one day, when PBS containing 2% casein was added to prepare a sensitization plate. At the time of ELISA determination, the above-mentioned solution was removed and the microplate was washed with PBS; the subject culture supernatant of hybridoma was then added and reaction was carried out at room temperature for 2 hr. After microplate washing with PBS, HRP-labeled goat anti-human Ig antibodies were added, and further reaction carried out at room temperature for 2 hr. Enzyme reaction was then carried out by the method described in Reference Example 2, and the antibody titer was determined.

REFERENCE EXAMPLE 4

EBV Transformant

Lymphocytes were separated from normal human peripheral blood by the specific gravity centrifugation method, using Ficoll-Hypaque, and suspended in Iskove-Ham medium containing 20% FCS (IH-20F) to a density of $1 \times 10^7$ lymphocytes/ml. To this suspension, an EBV-containing culture supernatant of B-95-8 cells was added in a ratio by volume of 10 to 1 of the suspension; infection was carried out at 37° C. for 1 hr while the mixture was shaken gently. After infection, the lymphocytes were seeded on a 96-well microplate at $2 \times 10^4$ lymphocytes per well, followed by 2 to 4 weeks of cultivation at 37° C. in a carbon dioxide incubator to yield a transformant. The transformant thus obtained was used for fusion with the AC-33 line.

EXAMPLE 1

(1) Establishment Of The Human B Lymphoblastoid Cell Line AC-33

The 6-TG-resistant human B lymphoblastoid cell line WI-L2, supplied by the Alton Jones Cell Science Center, USA, was first cultivated in an Iskove-Ham medium (IH-10F) containing 10% FCS supplemented with 0.003 μM ouabain. From the line of cells found to be resistant to the low concentration of ouabain, cells which were not immunoglobulin secretors were selected. The selected cells were further cultivated in the presence of ouabain at stepwise increased concentrations of 0.005 μM, 0.01 μM, 0.02 μM, 0.05 μM, 0.15 μM, 0.5 μM, and 1 μM, whereby cells which were not immunoglobulin secretors were repeatedly selected. As the final result, the AC-33 line (FERM BP-2143, IFO 50155) was obtained, which exhibits resistance to 2 μM ouabain and which is not an immunoglobulin secretor.

(2) Chromosome Analysis Of The AC-33 Line

Chromosome analysis was conducted on the non-immunoglobulin secreting, HAT-sensitive, ouabain-resistant AC-33 line (FERM BP-2143, IFO 50155) obtained in Example 1 (1).

About $10^6$ cells were suspended in 10 ml of a proliferation medium containing 2 μg/ml colchicine (Wako Pure Chemical Industries, Ltd., Japan) and cultivated at 37° C. for 1.5 hr. The cells were then centrifuged at $250 \times g$ for 10 min.; the resulting sediment was suspended in 3 ml of 75 mM KCl and kept standing at 24° C. for 15 min. The cells were then washed twice with a fixation liquid (acetic acid: methanol = 1:3) by the centrifugal method, after which they were suspended in several drops of the same fixation liquid, placed on a slide glass, and air-dried. The specimen thus obtained was stained with Giemsa's stain and observed microscopically (Giemsa's method). This stained specimen, after being destained with the same fixation liquid, was treated with a phosphate buffer solution (PBS, pH 5.8) containing 0.02% trypsin (GIBCO Laboratories) at 0° C. for 6 min., after which it was washed with PBS, stained again with Giemsa's stain, and observed microscopically (G-band method).

The results are shown in FIG. 1.

As is evident from FIG. 1, the AC-33 line had 46 chromosomes, XY, and exhibited characteristics different from the TAW-925 line [Biochemical and Biophysical Research Communications, 142, 805 (1987)] at loci 3, 12, 20, and 22.

(3) Cell Fusion Of The AC-33 Line and EBV Transformant

The EBV transformant obtained in Reference Example 4 and the AC-33 line were mixed together in a cell ratio of 1 to 1, and treated with 45% PEG 6000 (Koch-Light Ltd.) for 7 min. to achieve cell fusion. After fusion, the transformant cells were suspended in an IH-10F medium to a concentration of $6 \times 10^3$, to $8 \times 10^4$ cells/ml. This suspension was seeded on a Linbro 24-well multidish at 1 ml per well, and cultivated at 37° C.

in a carbon dioxide incubator. Twenty-four hours later, 1 ml of an IH-10F medium containing HAT.ouabain ($1 \times 10^{-4}$M hypoxanthine, $4 \times 10^{-7}$M aminopterin, $1.6 \times 10^{-5}$M thymidine, $2 \times 10^{-6}$M ouabain) (HATO medium) was added to initiate HATO selective cultivation. At days 3, 5, and 7, as counted from the first day of medium addition, the old medium was replaced with 1 ml of fresh medium, and HATO selective cultivation was continued.

The results are shown in Table 1.

For comparison, the TAW-925 line [Biochemical and Biophysical Research Communications, 142, 805 (1987)] was used as the parental line to conduct the same experiment.

In the case of the AC-33 line, hybridoma proliferation was noted 9 to 15 days after cell fusion, the fusion efficiency (number of wells in which cell proliferation occurred/number of wells in which fused cells were seeded) being 59 to 100% for the four kinds of EBV transformants, with a means ± standard deviation of $85 \pm 16$%. On the other hand, in the case of the TAW-925 line, which is considered to provide a good fusion, the fusion efficiency obtained was 41 to 81% for the four kinds of EBV transformants, with a mean ± standard deviation of $63 \pm 17$%.

TABLE 1

| Parental line | EBV transformant type[1] | Number of seeded cells[2] | Number of wells seeded | Number of wells in which cells proliferated | Fusion efficiency |
|---|---|---|---|---|---|
| AC-33 line | A | $4 \times 10^4$ | 96 | 90 | 94% |
| | B | $3 \times 10^4$ | 96 | 95 | 99% |
| | B | $1.5 \times 10^4$ | 184 | 109 | 59% |
| | C | $3 \times 10^4$ | 96 | 72 | 75% |
| | D | $4 \times 10^4$ | 288 | 288 | 100% |
| | | | | Mean ± standard deviation | $85 \pm 16$% |
| TAW-925 line | A | $4 \times 10^4$ | 192 | 156 | 81% |
| | B | $3 \times 10^4$ | 96 | 45 | 47% |
| | B | $1.5 \times 10^4$ | 184 | 123 | 67% |
| | C | $3 \times 10^4$ | 184 | 76 | 41% |
| | D | $4 \times 10^4$ | 96 | 77 | 80% |
| | | | | Mean ± standard deviation | $63 \pm 17$% |

EXAMPLE 2

Obtaining An Anti-PEA Antibody-Producing Hybridoma

Human peripheral blood lymphocytes (PBL) positive for anti-PEA antibody were transformed by the method described in Reference Example 4 to prepare an anti-PEA antibody-producing EBV transformant. This transformant and the AC-33 line were then fused together by the method described in Example 1 (3), followed by HATO selective cultivation. Hybridoma proliferation was noted in 729 of the 944 wells in which cells were seeded, 9 to 15 days after cell fusion. The anti-PEA antibody in each culture supernatant was determined by ELISA as described in Reference Example 3. The anti-PEA antibody was detected in the culture supernatants of all 729 wells.

EXAMPLE 3

Cloning Of Anti-PEA Antibody-Producing Hybridoma

The hybridomas in the two wells positive for the antibody activity obtained in Example 2 (PA-1, PA-10) were each subjected to cloning by limiting dilution analysis. That is, each hybridoma was suspended in IH-10F medium to 3 hybridoma cells/ml; this suspension was then dispensed to a 96-well microplate at 0.1 ml per well. On dispensation, BALB/C mouse thymocytes, as feeder cells, were added to the microplate, at $5 \times 10^5$ cells per well. About 10 to 15 days later, cell proliferation was noted; the supernatant was collected and assayed for antibodies by ELISA, as described in Reference Example 3. Strong antibody activities were noted in all the 40 clones obtained from PA-1 and PA-10. Judging from this finding, it is evident that the hybridoma of the present invention is excellent in proliferativity and antibody productivity. From the above clones, the human-human hybridoma PA-10.1, particularly excellent in proliferativity and antibody productivity, was selected and bred (FERM BP-2146, IFO 50158).

EXAMPLE 4

Production Of Monoclonal Antibody

The human-human hybridoma PA-10.1 (FERM BP-2146, IFO 50158) was suspended in GIT medium (Daigo Eiyo Kagaku Co., Japan), followed by continuous cultivation at 37° C., with a stepwise increased cultivation volume. To 6 l of the culture supernatant thus obtained, ammonium sulfate was added, to a 47% concentration. This mixture was subjected to salting-out at 4° C. for 60 min. while stirring, after which it was centrifuged at 10,000 rpm for 15 min. The resulting precipitate was dissolved in a 20 mM Tris buffer solution (pH 7.9) containing 50 mM NaCl, and dialyzed against 1 l of the same buffer solution. Two hours later, the dialyzation liquid was replaced with a fresh liquid, and dialyzation was conducted for 15 more hours, followed by centrifugation at 10,000 rpm for 15 min. The supernatant was applied to a 10-ml DEAE-cellulose column (Whatman DE52) equilibrated with a Tris buffer solution containing 50 mM NaCl; the effluent fraction which passed through the column, in elution with a Tris buffer solution containing 50 mM NaCl, was concentrated to yield the monoclonal antibody PA-10.1. Antibody purity was confirmed by 10% SDS-polyacrylamide gel electrophoresis, in accordance with the method of Laemli et al. [Nature, 227, 580 (1970)]. That is, the fraction which passed through the DEAE-cellulose column after salting-out with ammonium sulfate was reduced with 2-mercaptoethanol and electrophoresed at 180 V for 22 hours. Two bands appeared: an H-chain band at the position corresponding to a molecular weight of about 52 kilodaltons, and an L-chain band at about 28 kilodaltons, but no band assigned to impurities was observed.

EXAMPLE 5

Obtaining And Cloning Anti-Cancer Antibody-Producting Hybridoma

Human PBLs were transformed, by the method described in Reference Example 4, to prepare an EBV transformant. This EBV transformant and the AC-33 line were fused together by the method described in Example 3; this was followed by HATO selective cultivation. After cell fusion, the cells were seeded in a microplate at a concentration of $4 \times 10^4$ to $6 \times 10^4$ cells/ml. The culture supernatants of the wells in which human-human hybridoma proliferation was noted 12 to 14 days later were subjected to the MHA and cell-ELISA tests described in Reference Examples 1 and 2, respectively.

For comparison, the TAW-925 line was used as the parental line to conduct the same experiment. The results are shown in Table 2.

In the case of the AC-33 line, fusion efficiency was 35% for the 7,851 wells in which cells were seeded; two kinds of anti-cancer antibody-producing hybridomas were obtained. In the case of the TAW-925 line, the fusion efficiency was 4 to 31% for the 48,239 wells in which cells were seeded, with a mean ± standard deviation of 18±8%; only one line of anti-cancer antibody-producing hybridoma was obtained. From the results shown in Table 2, it is evident that the AC-33 line is excellent in fusion efficiency, and can therefore be used advantageously to obtain an anti-cancer antibody-producing hybridoma.

As stated above, in the fusion experiment using the AC-33 line as the parental line, one well exhibiting binding affinity to the gastric cancer cell line AZ-521 and the lung cancer cell line CADO-LC3, and another well exhibiting binding affinity to the liver cancer cell lines HEP-G2 and hu-H4 were obtained. The hybridomas in these two wells were subjected to cloning by limiting dilution analysis, and the cloned hybridoma cells were seeded in microplate wells in the presence of thymocytes as feeder cells in the same manner as described in Example 5. About 2 weeks later, the antibody titer of the supernatant of each of the wells in which cell proliferation was noted was determined by MHA and cell-ELISA, whereby human-human hybridomas excellent in proliferativity and antibody productivity were selected and bred.

As a result, the human-human hybridoma Ku102, producing an antibody reactive to AZ-521 and CADO-LC3, and the human-human hybridoma Ku105, producing an antibody reactive to HEP-G2 and hu-H4, were respectively obtained (FERM BP-2144, IFO 50156 and FERM BP-2145, IFO 50157, respectively).

TABLE 2

| Parental line | Experiment number | Number of wells seeded | Number of wells in which cells proliferated | Fusion efficiency | Number of wells positive for anti-cancer antibody |
|---|---|---|---|---|---|
| AC-33 line | 1 | 7,851 | 2,778 | 35% | 2 |
| TAW-925 line | 1 | 9,123 | 2,855 | 31% | 1 |
|  | 2 | 6,623 | 1,330 | 20% | 0 |
|  | 3 | 8,874 | 1,268 | 14% | 0 |
|  | 4 | 6,977 | 1,648 | 24% | 0 |
|  | 5 | 4,176 | 550 | 13% | 0 |
|  | 6 | 9,826 | 1,624 | 17% | 0 |
|  | 7 | 2,640 | 115 | 4% | 0 |
|  | Total | 48,239 | 9,390 | 18 ± 8%[1] | 1 |

Note:
[1] Mean ± standard deviation

What is claimed is:

1. Human B lymphoblastoid cell line FERM BP-2143 or a subculture line of cell line FERM BP-2143.

* * * * *